United States Patent [19]
Grabek

[11] Patent Number: 5,931,810
[45] Date of Patent: *Aug. 3, 1999

[54] METHOD FOR ACCESSING THE PERICARDIAL SPACE

[75] Inventor: James R. Grabek, Long Lake, Minn.

[73] Assignee: Comedicus Incorporated, Columbia Heights, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/761,189

[22] Filed: Dec. 5, 1996

[51] Int. Cl.$^6$ .................................................. A61M 25/06
[52] U.S. Cl. .............................. 604/51; 604/115; 606/205
[58] Field of Search ................................. 606/205, 129; 604/51, 115, 158

[56] References Cited

U.S. PATENT DOCUMENTS

| | | |
|---|---|---|
| 3,923,060 | 12/1975 | Ellinwood, Jr. . |
| 4,003,379 | 1/1977 | Ellinwood, Jr. . |
| 4,027,510 | 6/1977 | Hiltebrandt . |
| 4,222,380 | 9/1980 | Terayama ............................. 604/115 |
| 4,620,547 | 11/1986 | Boebel . |
| 4,656,999 | 8/1987 | Storz . |
| 4,759,348 | 7/1988 | Cawood . |
| 4,991,578 | 2/1991 | Cohen . |
| 5,033,477 | 7/1991 | Chin et al. . |
| 5,071,412 | 12/1991 | Noda . |
| 5,071,428 | 12/1991 | Chin et al. ............................. 606/184 |
| 5,213,570 | 5/1993 | VanDeripe . |
| 5,220,917 | 6/1993 | Cammilli et al. . |
| 5,235,966 | 8/1993 | Jamner . |

(List continued on next page.)

FOREIGN PATENT DOCUMENTS

| | | |
|---|---|---|
| 0 417 031 A2 | 3/1991 | European Pat. Off. . |
| 0 706 781 A2 | 4/1996 | European Pat. Off. . |
| WO 95/17919 | 7/1995 | WIPO . |
| WO 96/22056 | 7/1996 | WIPO . |
| WO 96/40368 | 12/1996 | WIPO . |
| WO 98/05289 | 2/1998 | WIPO . |

OTHER PUBLICATIONS

PCT International Search Report Apr. 14, 1998.
Medical Devices & Diagnostic Industry, Advertisement, "Spectrum . . . precision from start to finish".
Product Description Sheet by COMEDICUS Incorporated for A New Approach: Access The Pericardial Space With The PerDUCER™ Pericardial Access Device.
Medical Device & Diagnostic Industry, Advertisement, "Spectrum . . . precision from start to finish".
Advertisement "Corrosion–Resistant Alloys", Ulbrich Stainless & Steels Special Metals Inc.
Surgical Instruments, Advertisement for T.A.G. Medical Products Ltd.
Catalog pages of Portlyn Medical Products, pp. 4, 24 and 25, (1997).

*Primary Examiner*—Michael H. Thaler
*Attorney, Agent, or Firm*—Merchant & Gould P.C.

[57] ABSTRACT

There is provided an apparatus and a method of using the apparatus for creating a bleb of tissue of the pericardium of the heart, for accessing the pericardial space, intermediate the pericardium and the heart, and withdrawing fluid therefrom or delivering fluid, including drugs, therapeutic agents, or the like, thereto. The apparatus of the present invention includes a shaft with a first distal end and a second proximal end. A bore extends through the shaft from the distal end to the proximal end. The first end includes jaws, that open and close, as at least one of the jaws is movable. The second end includes a handle, at least a portion of the handle in communication with a mechanism in communication with the movable jaw, such that upon movement of at least a portion of the handle, the jaws can be opened and closed continuously. A needle, for puncturing the bleb of tissue grasped within the jaws, is movably mounted within the bore and is in communication with a mechanism for limiting its travel with respect to the bore.

9 Claims, 4 Drawing Sheets

U.S. PATENT DOCUMENTS

| | | | |
|---|---|---|---|
| 5,249,574 | 10/1993 | Bush et al. . | |
| 5,281,230 | 1/1994 | Heidmueller | 606/205 X |
| 5,290,299 | 3/1994 | Fain et al. . | |
| 5,318,589 | 6/1994 | Lichtman | 606/205 |
| 5,336,252 | 8/1994 | Cohen . | |
| 5,387,419 | 2/1995 | Levy et al. . | |
| 5,496,310 | 3/1996 | Exconde et al. . | |
| 5,536,251 | 7/1996 | Evard et al. | 604/93 |

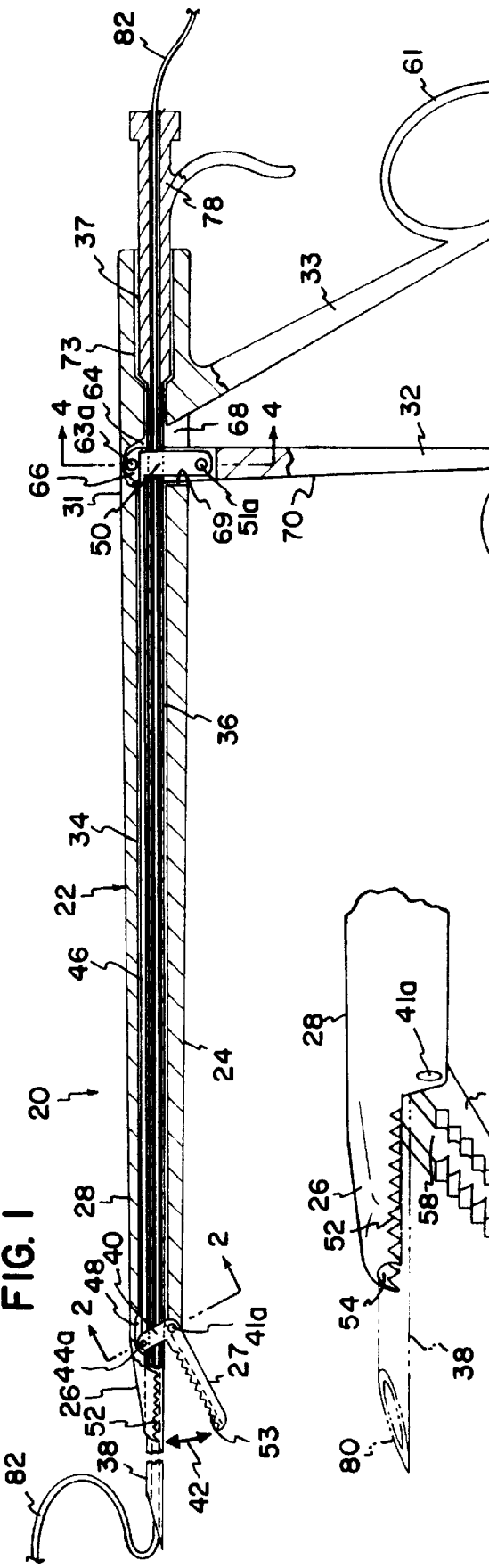
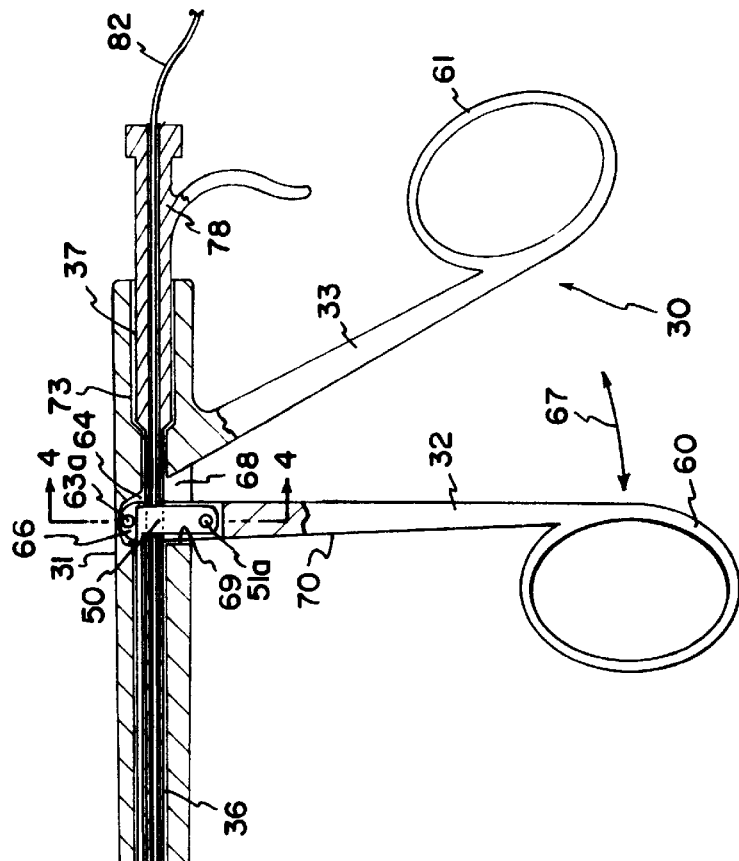
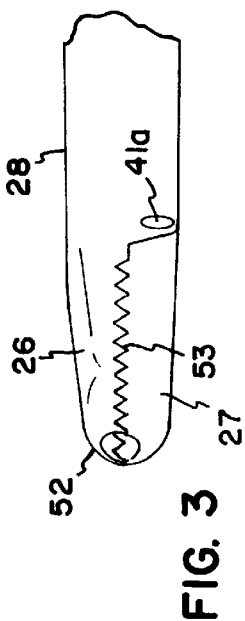
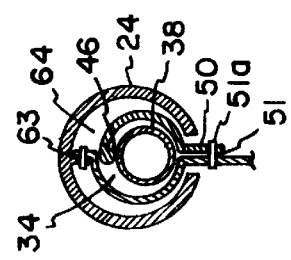

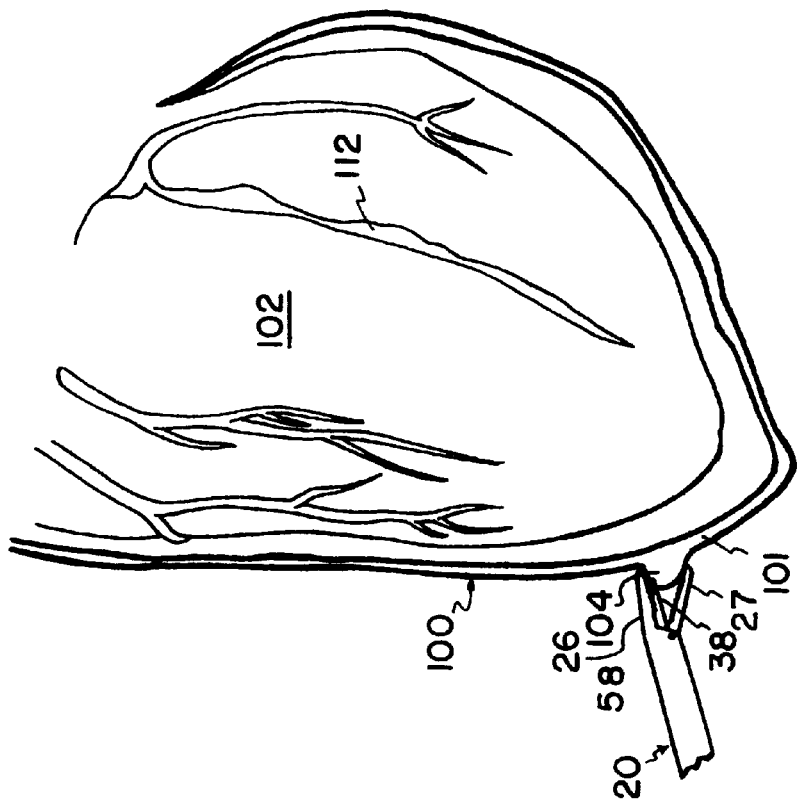
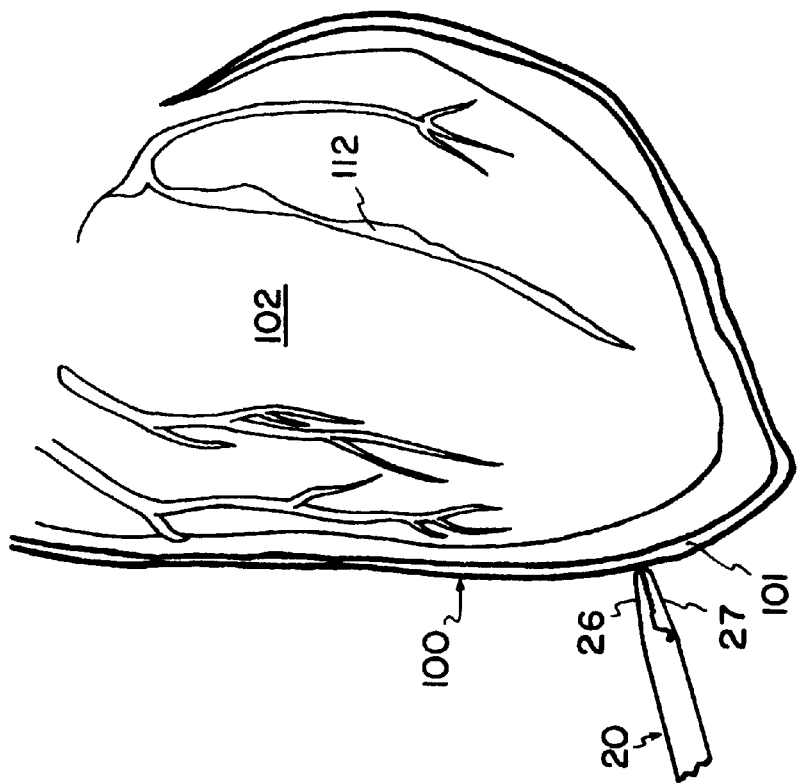

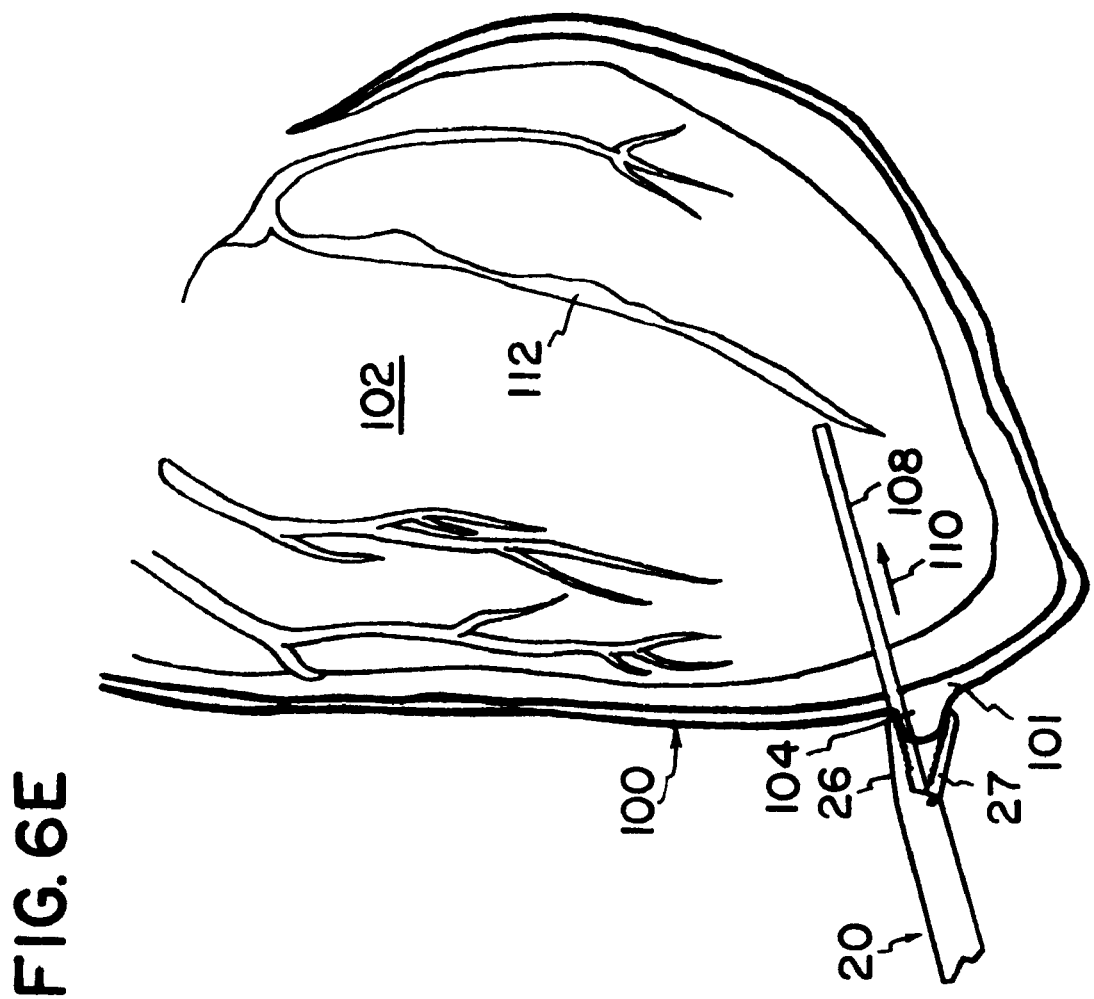

METHOD FOR ACCESSING THE PERICARDIAL SPACE

FIELD OF THE INVENTION

The present invention is directed to treating the heart muscle and associated coronary vessels by providing access to the pericardial space between the heart and the pericardium (pericardial sac), without injuring the heart and associated coronary vessels. In particular, the present invention is directed to a device and method for safely accessing the pericardial space and directly infusing fluids including drugs therein or removing fluid(s) directly therefrom.

BACKGROUND OF THE INVENTION

Knowledge of the pericardium (pericardial sac) dates back to the time of Galen (129–200 A.D.) the Greek physician and anatomist who created the term "pericardium." The pericardium (pericardial sac) is a conical membranous sac in which the heart and the commencement of the great vessels are contained. Gray's Anatomy (1977 ed.) pp. 457–460. The pericardium is fluid-filled and functions to prevent dilation of the chambers of the heart, lubricates the surfaces of the heart, and maintains the heart in a fixed geometric position. It also provides a barrier to the spread of infection from adjacent structures in the chest cavity and prevents surrounding tissue(s) from adhering to the heart. The space between the pericardium and the heart, known as the pericardial space, is normally small in volume and includes the fluid therein. It has been reported by others that when fluid is injected into the pericardial space it accumulates in the atrioventricular and interventricular grooves, but not over the ventricular surfaces. See, Shabetai R, "Pericardial and Cardiac Pressure", in *Circulation*, 77:1 (1988).

Pericardiocentesis, or puncture of the pericardium, heretofore has been performed for; 1) diagnosis of pericardial disease(s) by study of the pericardial fluid; 2) withdrawal of pericardial fluid for the treatment of acute cardiac tamponade; and 3) infusion of therapeutic agents for the treatment of malignant effusion or tumors. During 1994, it was estimated that approximately 12,000 pericardiocentesis procedures were performed in the United States and that less than 200 of these patients underwent therapy with the intrapericardial injection of drugs. At present, intrapericardial injection of drugs is clinically limited to the treatment of abnormal pericardial conditions and diseases, such as malignant or loculated pericardial effusions and tumors. Drugs that have been injected into the pericardial space include antibiotic (sclerosing) agents, such as tetracycline, bleomycin and streptokinase.

Intrapericardial drug delivery has not been clinically utilized for heart-specific treatments where pericardial pathology is normal, because the pericardial space is normally small and very difficult to access without invasive surgery or risk of cardiac injury by standard needle pericardiocentesis techniques. Normally, pericardiocentesis procedures are carried out by highly specialized, experienced personnel in the cardiac catheterization laboratory of medical facilities, assisted by fluoroscopy and electrocardiogram monitoring equipment. Electrocardiographic monitoring of pericardiocentesis, using the pericardial needle as an electrode is commonly employed, as disclosed in Bishop L. H., et al., "The Electrocardiogram as a Safeguard in Pericardiocentesis", in *JAMA*, 162:264 (1956), and Neill J. R., et al., "A Pericardiocentesis Electrode", in *The New England Journal of Medicine*, 264:711 (1961); Gotsman M. S., et al. "A Pericardiocentesis Electrode Needle", in *Br. Heart J.*, 28:566 (1966); and Kerber R. E., et al., "Electrocardiographic Indications of Atrial Puncture During Pericardiocentesis", in *The New England Journal of Medicine*, 282:1142 (1970). An echocardiographic transducer with a central lumen has also been used to guide the pericardiocentesis needle, as reported in Goldberg B. B., et al., "Ultrasonically Guided Pericardiocentesis", in *Amer. J. Cardiol.*, 31:490 (1973).

However, there are complications associated with needle pericardiocentesis. These complications include laceration of a coronary artery or the right ventricle, perforation of the right atrium or ventricle, puncture of the stomach or colon, pneumothorax, arrhythmia, tamponade, hypertension, ventricular fibrillation, and death. Complication rates for needle pericardiocentesis are increased in situations where the pericardial space and fluid effusion volume is small (i.e. the pericardial size is more like normal and not abnormally distended by the accumulation of fluid, e.g., blood).

U.S. Pat. No. 5,071,428 (Chin, et al.) discloses a method and apparatus for accessing the pericardial space for the insertion of implantable defibrillation leads. This method requires griping the pericardium with a forceps device and cutting the pericardium with a scalpel (pericardiotomy) under direct vision through a subxiphoid surgical incision.

Uchida Y., et al., "Angiogenic Therapy of Acute Myocardial Infarction by Intrapericardial Injection of Basic Fibroblast Growth Factor and Heparin Sulfate", in *Circulation AHA Abstracts* (1994), reported a method for the intrapericardial injection of angiogenic agents. While not described in detail, this method generally involved the percutaneous transcatheter bolus injection of drugs into the pericardial cavity via the right atrium. A major drawback of this method is that the right atrial wall is crossed, that could lead to bleeding into the pericardial space. In addition, the method involved the bolus injection of drugs rather than long-term delivery via a catheter or controlled release material.

Another method for intrapericardial injection of agents is performed by a device, available under the name PerDUCER™ pericardial access device, available from Comedicus Incorporated, 3839 Central Avenue, NE, Columbia Heights, Minn. 55421. This device creates a lifted section of the pericardium, known as a "bleb" through suction. Specifically, the bleb is secured in an instrument end by suction, and the tissue forming the bleb in this end takes the shape of the instrument end. The bleb is then punctured by a needle of limited travel, and a guidewire is inserted into the bleb. A fluid infusion catheter is then moved over the guidewire, for example, to aspirate fluids from or deliver therapeutic drugs to the pericardium, pericardial space or heart muscle, via the bleb.

SUMMARY OF THE INVENTION

The present invention provides an alternate method of manually creating a controlled bleb. The present invention allows for safe access to the pericardial space without injury to the heart, in order to aspirate fluids directly from or to directly deliver fluids, i.e., therapeutic drugs, to the heart muscle. With such safe access to the heart, complications from contacting the heart muscle are greatly reduced and nearly eliminated. Additionally, by directly delivering drugs to the heart muscle via the pericardium (pericardial sac), side affects associated with drug delivery by conventional administration methods, i.e., oral or injection, can be reduced, such that lesser dosages are needed to achieve the desired effect of a specific drug. Moreover, this direct method of drug delivery allows for a wider range of drugs to be used.

The apparatus of the present invention includes a shaft with a first distal end and a second proximal end. A bore extends through the shaft from the distal end to the proximal end. The first end includes jaws, that open and close, as at least one of the jaws is movable. The second end includes a handle, at least a portion of the handle in communication with a mechanism in communication with the movable jaw, such that upon movement of at least a portion of the handle, the jaws can be opened and closed at will and to any desired degree. A needle, for puncturing tissue (e.g., a bleb of pericardium tissue), grasped within the jaws, is movably mounted within the bore and is in communication with a mechanism for limiting its travel with respect to the bore.

The present invention additionally includes a method for mechanically creating a bleb of pericardium tissue, with the apparatus of the present invention, and subsequently accessing the pericardial space. This access includes the use of guidewires, catheters, and other instrumentation.

BRIEF DESCRIPTION OF THE DRAWINGS

The present invention will be described with reference to the accompanying drawings, wherein like reference numerals identify corresponding or like components.

In the drawings:

FIG. 1 is a side view and with a partial cross-sectional view of the apparatus of the present invention;

FIG. 2 is a cross-sectional view of the apparatus of the present invention taken along line 2–2 of FIG. 1;

FIG. 3 is a is a perspective view of the first or distal and of the apparatus with the jaws closed;

FIG. 4 is a cross-sectional view of the apparatus of the present invention taken along line 4–4 of FIG. 1;

FIG. 5 is a perspective view of the first or distal and of the apparatus with the jaws open; and FIGS. 6A–6E are perspective views detailing the apparatus of the present invention performing the method of the present invention.

DETAILED DESCRIPTION OF THE DRAWINGS

Figure 6D:
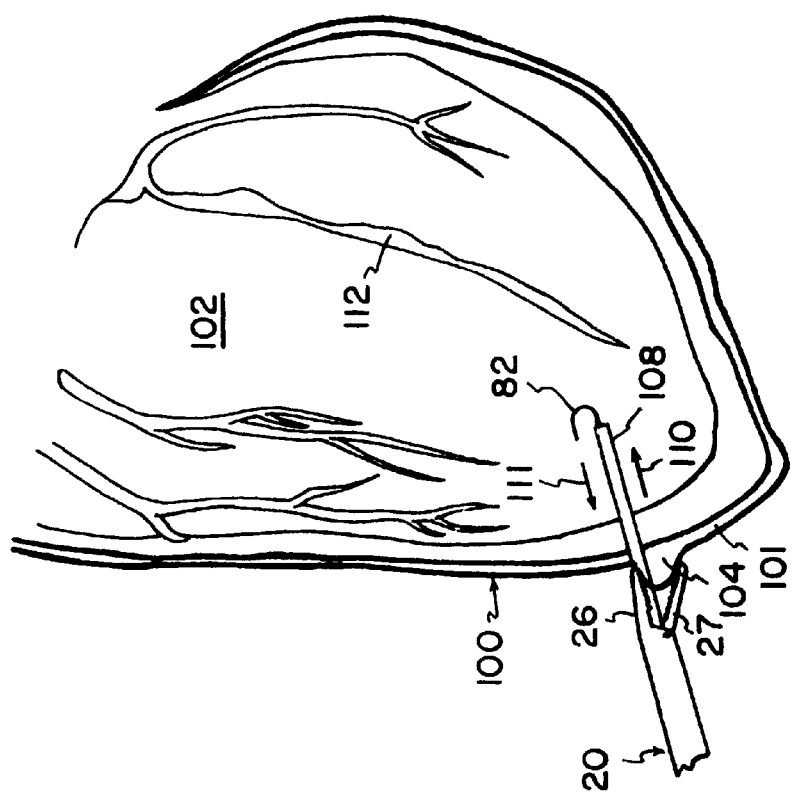

FIGS. 1–5 detail the apparatus 20 of the present invention. The apparatus includes a body 22 having a shaft 24 with jaws 26, 27 at a first or distal end 28 and a handle 30, at a second or proximal end 31, the handle 30 formed of a movable arm 32 and a fixed arm 33. The shaft 24 has a bore 34 extending therethrough, with distal 36 and proximal 37 portions, to accommodate a needle 38 and additional structures for fluid aspiration or infusion (detailed below) from or to the pericardial space 101 (FIGS. 6A–6E).

A first jaw 26 and a second jaw 27 are at the first end 28 of the shaft 24, with the second jaw 27 being movable, as it is piviotally mounted to the body 22 of the shaft 24, by a hinge 40 at pins 41 at pivot points 41a. This hinge 40, and subsequent attachments (detailed below), allow the second (movable) jaw 27, to be moved in the direction of the arrow 42, such that the jaws 26, 27 are closed and opened when desired, to any desired degree.

The hinge 40, as shown in FIG. 2, is preferably an arc-like piece, of a curvature conforming to that of the bore 34, and attaches by a pin 44 or the like at a second pivot point 44a to a rod 46. The second pivot point 44a moves within a well 48, cut into the body 22 of the shaft 24. The rod 46 terminates in a flange 50, piviotally mounted to the movable arm 32 at by a pin 51 at a pivot point 51a. Movement from the movable arm 32 moves the rod 46 (forward, toward the first end 28 of the shaft 24, or backward, toward the second end 34 of the shaft 24) within the bore 34, to ultimately move the jaws 26, 27 between the closed and open positions (in the direction of the arrow 42), to the degree desired by the operator.

The jaws 26, 27 include cooperatingly arranged, preferably correspondingly configured, teeth 52, 53, in order to assist the jaws 26, 27, when brought together, to sufficiently grasp and retain tissue (i.e., the tissue of the pericardium, also known as the pericardial sac, forming the bleb). The teeth 52, 53 are preferably of a uniform pitch (as shown in the drawing figures) for the entire length of their respective jaws 26, 27, but could be of different pitches provided they remain cooperatingly arranged on each jaw 26, 27 and that the jaws 26, 27 remain able to close completely (FIG. 3). The jaws 26, 27 also include grooves 54, 55, for assisting in the gripping and traction on the tissue of the bleb without damaging it, as well as accommodating the needle and other related instrumentation, as discussed below. Additionally, it is preferred that the jaws 26, 27 be shaped such that upon incomplete closure (e.g., during the grasping and retaining of tissue) or complete closure (e.g., when the apparatus 20 is being moved into the body), there is a cavity 58 between them, for receiving tissue of the pericardium.

While two jaws 26, 27 are preferred, arrangements of more than two jaws are also permissible, provided their arrangement allows for sufficient grip and manipulation of tissue.

At the handle 30, the second end 32 of the shaft 24, is formed of the movable 32 and fixed 33 arms. The fixed arm 33 extends from the body 22 at an angle (approximately 60 degrees). Both arms 32, 33 terminate in loops 60, 61, to accommodate the fingers of an operator. While loops 60, 61 are preferred, other equivalent structures, such as crescent-shaped members or the like are also permissible.

The movable arm 32 is piviotally mounted to the body 22 of the shaft 24 by a pin 63 or the like at a point 63a, within a slot 64 cut into the body 22. It is preferred that the terminal edge 66 of this movable arm be rounded, so as to allow for movement (toward the distal 28 and proximal ends 32 of the shaft 24) of the movable arm 32 in the direction of the arrow 67, as the movable arm 32 is free to travel within a space 68 in the body 22 of the shaft. Travel of the movable arm 32 is confined to this space 68, by the abutment of the surface 69 of the body 22 and the surface of the movable arm 70, and the fixed arm 33. It is also preferred that the flange 50 be on one side of the bore 36, while the portion of the movable arm 32 within the body 22 be on the other side, so as to straddle the needle 38 or other instrumentation in the bore 34, as shown in detail in FIG. 4. It is also preferred that portions of the flange 50 and movable arm 32 within the body 22, be of a diameter as close as possible to that of the bore 34, to allow for unobstructed passage of the needle 38 or other instrumentation through the bore 34.

The movable arm 32 is preferably not biased, such that the ultimate position of the jaws 26, 27 (open or closed, as desired by the operator) depends on the position of the movable arm 32. In alternate embodiments, the movable arm 32, hinge 40, rod 46 or flange 50 may be biased by springs or other equivalent mechanisms, such that the jaws 26, 27 are either open or closed when the apparatus 20 is not in use.

The shaft 24, jaws, 26, 27 handle 30 and components controlling the movement of the jaws 26, 27 (rod 46 and flange 50) are preferably made of titanium, stainless steel or the like. Plastics, such as polycarbonate, polyamide, acrylonitrile/butadiene/styrene (ABS) copolymers, or the like, can also be used.

The body 22 is preferably tubular in shape and the bore 34, is preferably circular in cross section. The proximal portion 37 of the bore 34 is of a diameter greater than that of the distal portion 36 of the bore 34. These distal 36 and proximal 37 portions are designed to accommodate the needle 38, needle trigger 78 (in the proximal portion 37 of the bore 34), guidewire(s) 82, catheter(s) 108 (FIGS. 6D and 6E) and other instrumentation that can be inserted into and moved through the bore 34.

The needle 38 is designed to extend past the jaws 26, 27 of the body 22 during use (if desired) (FIG. 5). However, movement of the needle is restricted by a needle trigger 78, preferably biased by a spring (not shown) that journals at least a portion of the needle 38 in the proximal portion 37 of the bore 34. The distal wall 73 of the proximal portion 37 of the bore 34, limits the travel of the needle trigger 78 (when it is activated by the operator), that ultimately limits the length of travel of the needle 38 in puncturing the bleb 104 (FIGS. 6B–6E).

The needle 38 is typically made of stainless steel or titanium and includes a beveled end 80, in order to produce a sharp precise puncture of the bleb 104. The needle is of a diameter less than that of the distal 36 and proximal portions of the bore 34, to slide within the bore 34, and is typically of a diameter of approximately 21 gauge (approximately 0.813 mm in diameter). The needle trigger 78 that surrounds a portion of the needle 38, is preferably made of TEFLON®, and is designed to slide within the proximal portion 37 of the bore 34. The needle 38 is preferably hollow, to accommodate guidewires 82, catheters 108 (FIGS. 6C–6E), catheter sheaths, catheter sheath introducers and other cannulation devices, to be moved (slid) through the needle 38 or the bore 34 (if the needle 38 has been removed), in order to, for example, aspirate fluid from the pericardial sac 101 (FIGS. 6A–6E) or deliver fluid, such as therapeutic drugs, to the pericardial sac 101.

Turning now to FIGS. 6A–6E, there is shown the apparatus 20 of the present invention in use for accessing the pericardium 100, and entering the pericardial space 101 surrounding the heart 102. Initially, a subxiphoid incision is made in the chest cavity of a patient. A standard mediastinscopy endoscope is inserted into this incision for direct vision and the apparatus 20 of the present invention is inserted through the endoscope. Once at a point proximate the tissue of the pericardium 100, such that the jaws 26, 27 apply a gentle pressure to the pericardium 100, as shown in FIG. 6A.

In FIG. 6B, the operator advances the movable arm 32 (FIG. 1) of the apparatus 20 toward the first or distal end 28 (FIG. 1) of the shaft 24 (FIG. 1), moving the jaw 27, and thus, opening the jaws 26, 27. Pericardium 100 tissue, as a result of back pressure exerted thereon, by the fluid in the pericardial space 101, now fills the cavity 58 (FIG. 1) between the jaws 26, 27 and the teeth 52, 53 (FIGS. 1, 3 and 5) of the jaws 26, 27 exert sufficient traction on the pericardium 100 tissue, such that upon incompletely closing of the jaws 26, 27 (as the operator moves the movable arm 32 back toward the second or proximal end 31 of the shaft 24, bringing the movable jaw 27 toward the other jaw 26), the pericardium 100 tissue is in the cavity 58, whereby a bleb 104 of pericardium 100 tissue has been created.

Figure 6C:
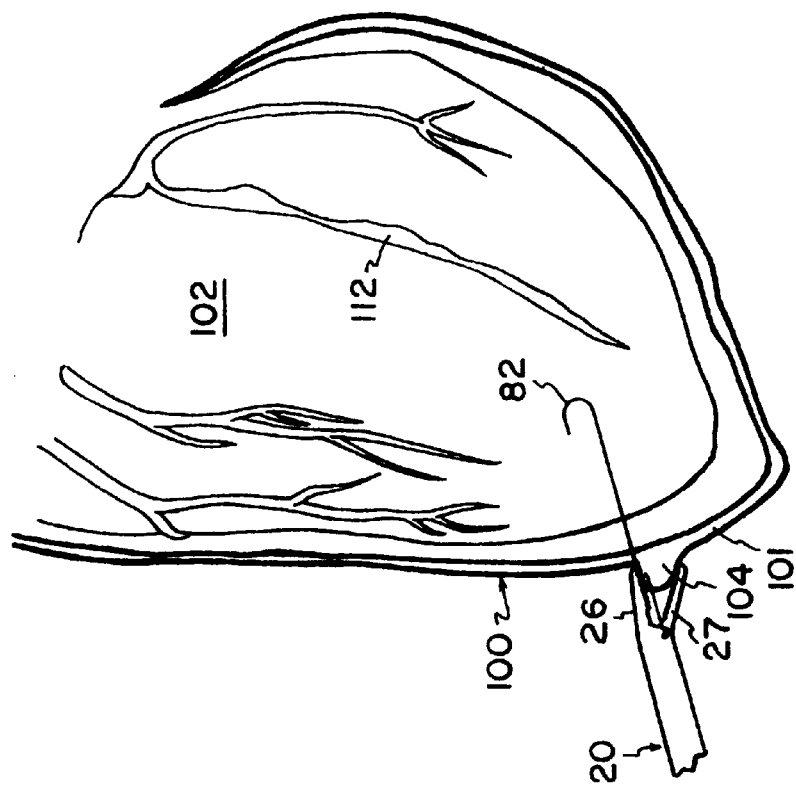

With the bleb 104 now established, in an optional step, the operator can move the apparatus 20 holding the bleb 104, in a direction away from the heart 102, to increase the size of the bleb 104. The operator activates the needle trigger 78, advancing the needle 38 toward the distal end 28 of the shaft 24 into the bleb 104, by puncturing the pericardium 100 tissue. This puncture is such that the needle 38 has safely entered the pericardial space 101 within the bleb 104 safely, without puncturing the heart 102. Upon puncture, the guidewire 82 is advanced through the needle 38 into the pericardial space 101 (FIG. 6C).

With the guidewire 82 now advanced into the pericardial space 101, a fluid retrieving or delivering catheter 108 can now be advanced over the guidewire 82 (in the direction of the arrow 110), as shown in FIG. 6D. Advancement of the catheter 108 (in the direction of arrow 110) continues simultaneous with withdrawal of the guidewire 82 (in the direction of arrow 111) until the catheter 108 is properly positioned within the pericardial space 101, as shown in FIG. 6E. This catheter 108 allows for fluid aspiration directly from or fluid (e.g., drugs, therapeutic agents or the like) delivery directly into the pericardial space 101. In the case of fluid delivery, there is provided a direct route for treating the heart 102 and associated coronary vessels 112.

While embodiments of the present invention have been described so as to enable one of skill in the art to practice the present invention, the preceding description is intended to be exemplary and should not be used to limit the scope of the invention, which should be determined by reference to the following claims.

What is claimed is:

1. A method for accessing the space between the pericardium and the heart, comprising:
    a) providing a pericardial access device including at least two jaws movable relative to each other, and means for accommodating instrumentation extending through said access device;
    b) mechanically grasping a portion of the pericardium between said at least two jaws of said access device;
    c) mechanically pulling said grasped portion of the pericardium away from the heart to form a bled of pericardium tissue adjacent said jaws;
    d) inserting a needle through said instrumentation accommodating means into said bleb, and limiting the travel of the needle to prevent laceration of the heart; and
    e) introducing a guidewire, through the needle into said bleb and into said pericardial space.

2. The method of claim 1, additionally comprising, introducing an instrument through said instrumentation accommodating means in said access device over said guidewire and into the pericardial space.

3. The method of claim 2, wherein said instrument is a catheter.

4. The method of claim 1, wherein said bleb is formed without suction.

5. A method for accessing the pericardial space, the method comprising a step of:

grasping an exterior surface of an unopened pericardium surrounding a patient's heart between at least two grasping surfaces of a grasping instrument to create a bleb of pericardium;

penetrating the bleb of pericardium with a piercing instrument which passes between the grasping surfaces to access the pericardial space.

6. A method according to claim 5 wherein the grasping surfaces of the grasping instrument provide a passage through which the piercing instrument can freely pass to penetrate the bleb of pericardium.

7. A method according to claim 5 wherein the grasping surfaces of the grasping instrument include teeth.

8. A method according to claim 5 wherein the grasping instrument includes a shaft having a bore therethrough, the bore providing for passage of the piercing instrument through the shaft of the grasping instrument and into the bleb of pericardium.

9. A method according to claim 8 wherein the shaft has a first end and a second end, the first end including a handle for operating the grasping surfaces of the grasping instrument.

* * * * *

UNITED STATES PATENT AND TRADEMARK OFFICE
CERTIFICATE OF CORRECTION

| | | |
|---|---|---|
| PATENT NO. | : 5,931,810 | Page 1 of 1 |
| DATED | : August 3, 1999 | |
| INVENTOR(S) | : Grabek | |

It is certified that error appears in the above-identified patent and that said Letters Patent is hereby corrected as shown below:

Title page, [73] Assignee: "Mich," should read --Minn.--

<u>Column 6,</u>
Line 56, claim 1: "bled" should read --bleb--

Signed and Sealed this

Thirty-first Day of July, 2001

*Attest:*

Nicholas P. Godici

NICHOLAS P. GODICI
*Attesting Officer*  *Acting Director of the United States Patent and Trademark Office*